(12) United States Patent
Piers et al.

(10) Patent No.: US 7,543,937 B2
(45) Date of Patent: *Jun. 9, 2009

(54) MULTIFOCAL OPHTHALMIC LENS

(75) Inventors: Patricia Ann Piers, Groningen (NL); Hendrik A. Weeber, Groningen (NL); Sverker Norrby, Leek (NL)

(73) Assignee: AMO Groningen B.V., Groningen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 12/055,588

(22) Filed: Mar. 26, 2008

(65) Prior Publication Data

US 2008/0198326 A1 Aug. 21, 2008

Related U.S. Application Data

(62) Division of application No. 11/426,196, filed on Jun. 23, 2006, now Pat. No. 7,377,641, which is a division of application No. 10/724,852, filed on Dec. 1, 2003.

(60) Provisional application No. 60/430,515, filed on Dec. 3, 2002.

(30) Foreign Application Priority Data

Nov. 29, 2002 (SE) ..................... 0203564

(51) Int. Cl.
*G02C 7/06* (2006.01)

(52) U.S. Cl. ............ 351/177; 351/161; 351/164; 351/168; 623/6.24

(58) Field of Classification Search ......... 351/159–177; 623/6.11–6.62

See application file for complete search history.

(56) References Cited

U.S. PATENT DOCUMENTS

| 5,050,981 A | 9/1991 | Roffman |
| 6,082,856 A | 7/2000 | Dunn et al. |
| 2007/0002444 A1* | 1/2007 | Piers et al. .................. 359/565 |

* cited by examiner

*Primary Examiner*—Darryl J Collins
(74) *Attorney, Agent, or Firm*—Abbott Medical Optics Inc.

(57) ABSTRACT

A method of designing a multifocal ophthalmic lens with one base focus and at least one additional focus, capable of reducing aberrations of the eye for at least one of the foci after its implantation, comprising the steps of: (i) characterizing at least one corneal surface as a mathematical model; (ii) calculating the resulting aberrations of said corneal surface(s) by employing said mathematical model; (iii) modeling the multifocal ophthalmic lens such that a wavefront arriving from an optical system comprising said lens and said at least one corneal surface obtains reduced aberrations for at least one of the foci. There is also disclosed a method of selecting a multifocal intraocular lens, a method of designing a multifocal ophthalmic lens based on corneal data from a group of patients, and a multifocal ophthalmic lens.

20 Claims, 4 Drawing Sheets

MULTIFOCAL OPHTHALMIC LENS

TECHNICAL FIELD OF THE INVENTION

Figure 1:
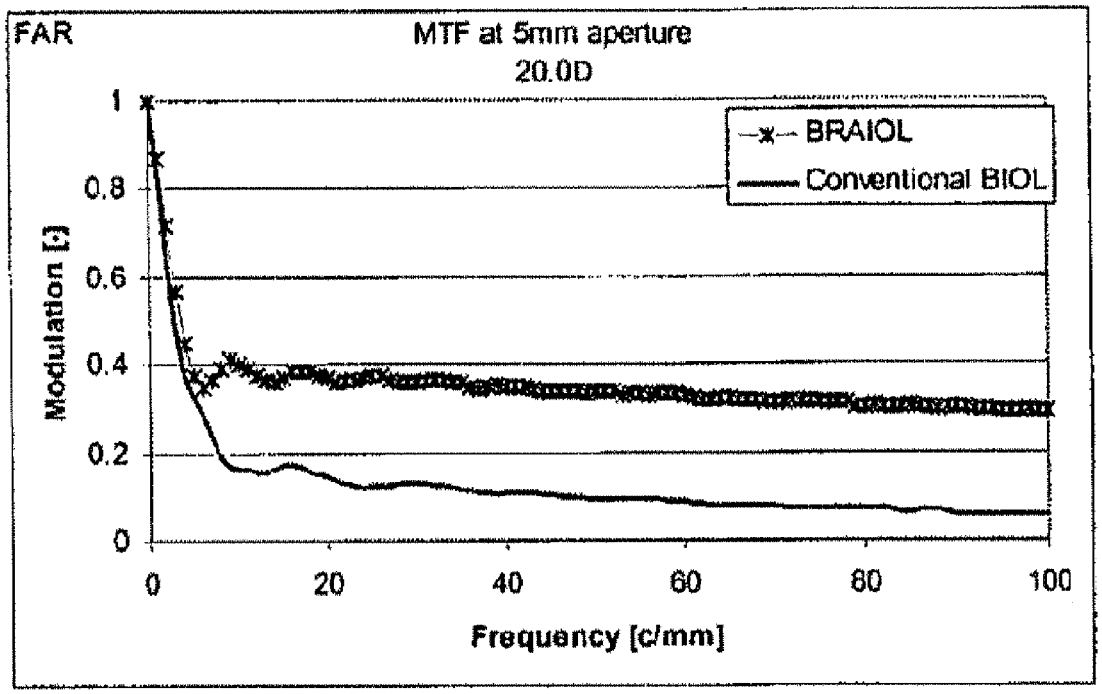
Figure 1:
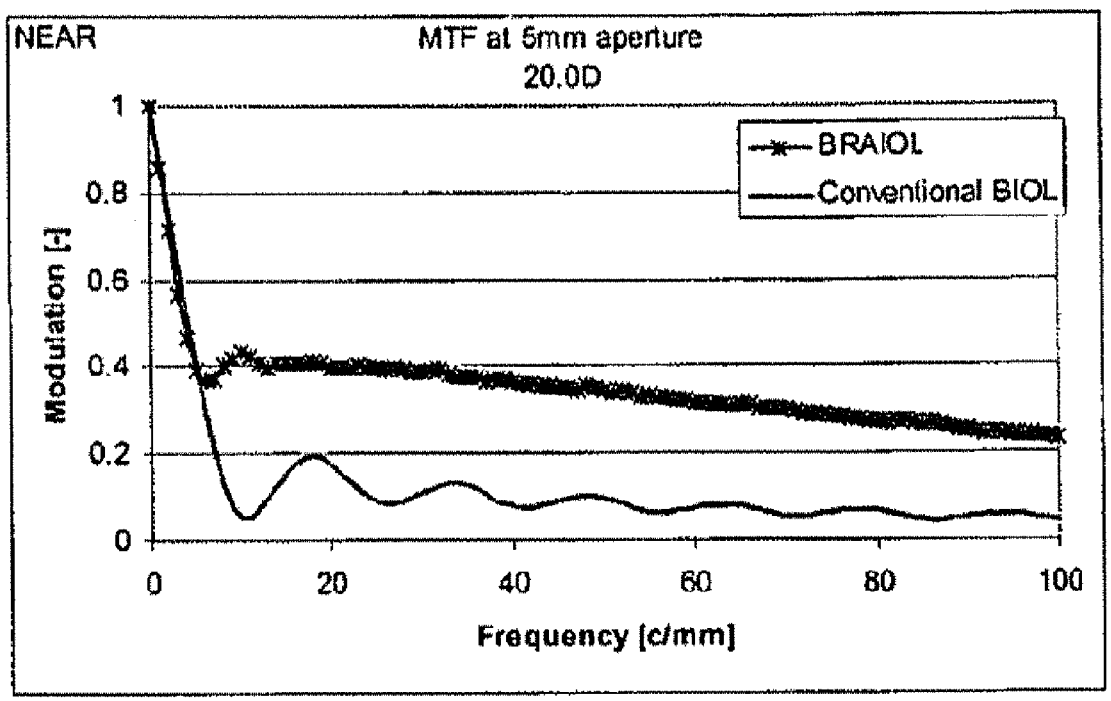

The present invention relates to a multifocal ophthalmic lens, and more in detail to a multifocal intraocular lens with reduced aberrations.

TECHNICAL BACKGROUND

Generally, a multifocal lens is required to provide a certain power for far vision and different, usually greater (more positive), powers for mid and near vision, the additional power for mid and near vision sometimes being referred to as "mid-add" and "near-add", which is usually expressed in dioptres. Multifocal lenses with two foci are referred to as bifocal.

Compared with monofocal ophthalmic lenses, multifocal ophthalmic lenses offer the advantage of reduced spectacle dependency, whereas patients with monofocal lenses generally need reading spectacles. In an ideal situation, the patient will have good vision in distance and near, while the depth of focus will enable vision in the intermediate. In this situation, the patient doesn't need spectacles in any situation. However, since a multifocal lens splits the available light into two or more foci, the visual quality in each focus is somewhat reduced. When a distant object is focused on the retina, a blurred image is superimposed due to the presence of the additional foci and vice versa, which obviously reduces the image quality. The reduced visual quality can be divided in reduced contrast sensitivity and appearance of optical phenomena, like straylight and halos. Moreover a patient has to undergo a learning period after implantation, as the two (or more) simultaneous images displayed on the retina can be confusing in the beginning. In most cases, the blurred image is discarded by the human visual perception and retinal processing system.

Usually, multifocal lenses are designed according to one or more of the following optical principles:

1. Diffractive type: conventional refractive lens combined with diffractive optics that splits light into two or more focal points.
2. Refractive optics with annular zones/rings with different radii of curvatures.

Examples of bifocal and multifocal intraocular lenses are disclosed in U.S. Pat. Nos. 4,642,112 and 5,089,024. Examples of commercially available multifocal lenses are: model CeeOn® model 811 E, Pharmacia, Kalamazoo, Mich. and SA 40, AMO, Irvine, Calif. The former is based on diffractive optics, whereby light is partitioned into two focal points, one for distance vision and one for near vision. The latter is a distance-dominant, zonal-progressive, multifocal optic with a 3.5-diopter near-add.

After IOL implantation, any remaining defocus (sphere) and astigmatism (cylinder) can be corrected by spectacles or contact lenses. Beside first order defocus and astigmatism of the eye a number of other vision defects could be present. For example aberrations of different orders occur when a wavefront passes a refracting surface. The wavefront itself becomes aspheric when it passes an optical surface that has imperfections, and vision defects occur when an aspheric wavefront falls on the retina. Both the cornea and the lens in the capsular bag contribute thus to these types of vision defects if they deviate from being perfect or perfectly compensating optical elements. The term aspheric will in this text include both asphericity and asymmetry. An aspheric surface could be either a rotationally symmetric or a rotationally asymmetric surface and/or an irregular surface, i.e. all surfaces not being spherical.

Recently, in studies on older subjects, it has been discovered that the visual quality of eyes having an implanted monofocal IOL, having spherical lens surfaces (hereafter referred to as a conventional intraocular lens (CIOL)) is comparable with normal eyes in a population of the same age. Consequently, a 70 year old cataract patient can only expect to obtain the visual quality of a non-cataracteous person of the same age after surgical implantation of an intraocular lens, although such lenses objectively have been regarded as optically superior to the natural crystalline lens. This result is explained by the fact that CIOLs are not adapted to, compensate for defects of the optical system of the human eye, namely optical aberrations.

In order to improve the performance of implanted intraocular lenses, efforts have been made to provide intraocular lenses for implantation that at least partly compensates for such aberrations (Reduced Aberration IOL, or RAIOL). The applicant's own application WO 01/89424 discloses an ophthalmic lens providing the eye with reduced aberrations, and a method of obtaining such. The method comprises the steps of characterizing at least one corneal surface as a mathematical model, calculating the resulting aberrations of said corneal surface(s) by employing said mathematical model, selecting the optical power of the intraocular lens. From this information, an ophthalmic lens is modeled so a wavefront arriving from an optical system comprising said lens and corneal model obtains reduced aberrations in the eye. The ophthalmic lenses as obtained by the methods are thus capable of reducing aberrations of the eye.

Of current multifocal lenses, the optical quality is lower than for current monofocal lenses. This shows in contrast sensitivity measurements on pseudophakic patients. As the visual quality of multifocal lenses is relatively low, even minor improvements in optical quality will lead to visible improvements.

Both WO 00/76426 and U.S. Pat. No. 6,457,826 mentions the possibility to make an aspheric BIOL. WO 00/76426 does not disclose use of any specific aspheric characteristic in the lens, but just mentions the possibility to combine an asphere with a diffractive pattern. However, U.S. Pat. No. 6,457,826 states that optical corrections can be made by aspherizing an IOL surface, but it is not at all described how this could be done.

In view of the foregoing, it is therefore apparent that there is a need for multifocal ophthalmic lenses that are better adapted to compensate the aberrations caused by the individual surfaces of the eye, such as the corneal surfaces, and capable of better correcting aberrations other than defocus and astigmatism, as is provided with conventional multifocal intraocular lenses.

SUMMARY OF THE INVENTION

The object of the invention is to provide a multifocal intraocular lens and a method of designing for designing such, which overcome the drawbacks of the prior art devices and methods. This is achieved by the method as defined in claims 1-20.

One advantage with the multifocal intraocular lens according to the present invention is the improved visual quality that can be obtained.

Embodiments of the invention are defined in the dependent claims.

SHORT DESCRIPTION OF THE FIGURES

FIG. 1 shows a calculated Modulation Transfer Function for a bifocal intraocular lens according to the present invention and a conventional bifocal lens.

Figure 2:
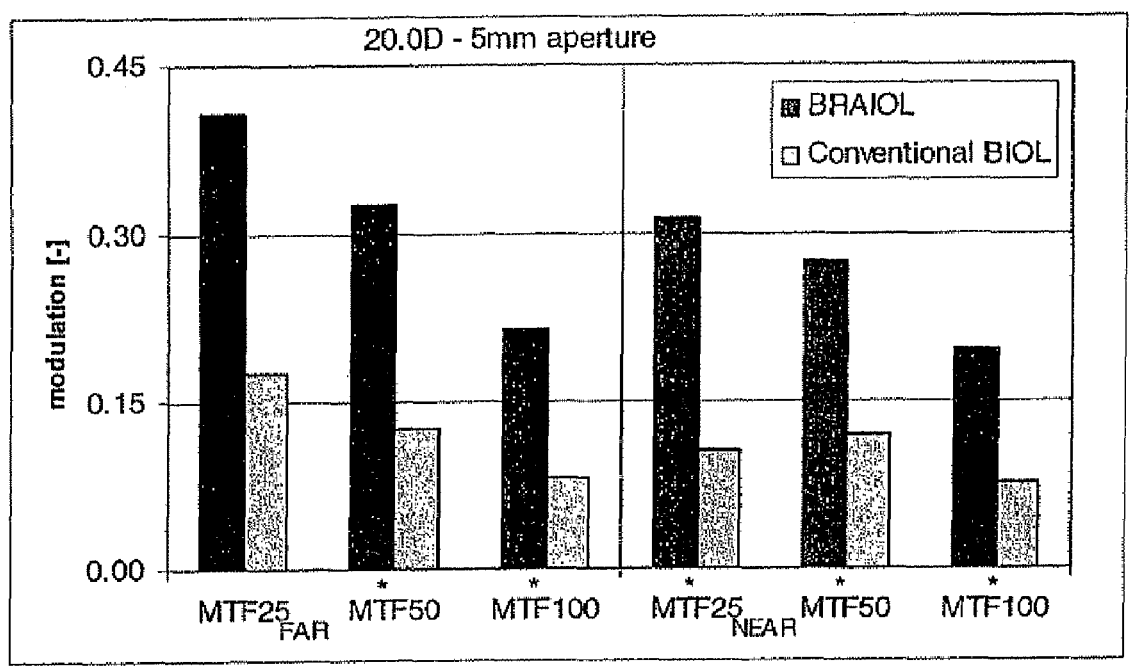

FIG. 2. shows a measured Modulation Transfer Function for a bifocal intraocular lens according to the present invention and a conventional bifocal lens.

Figure 3:
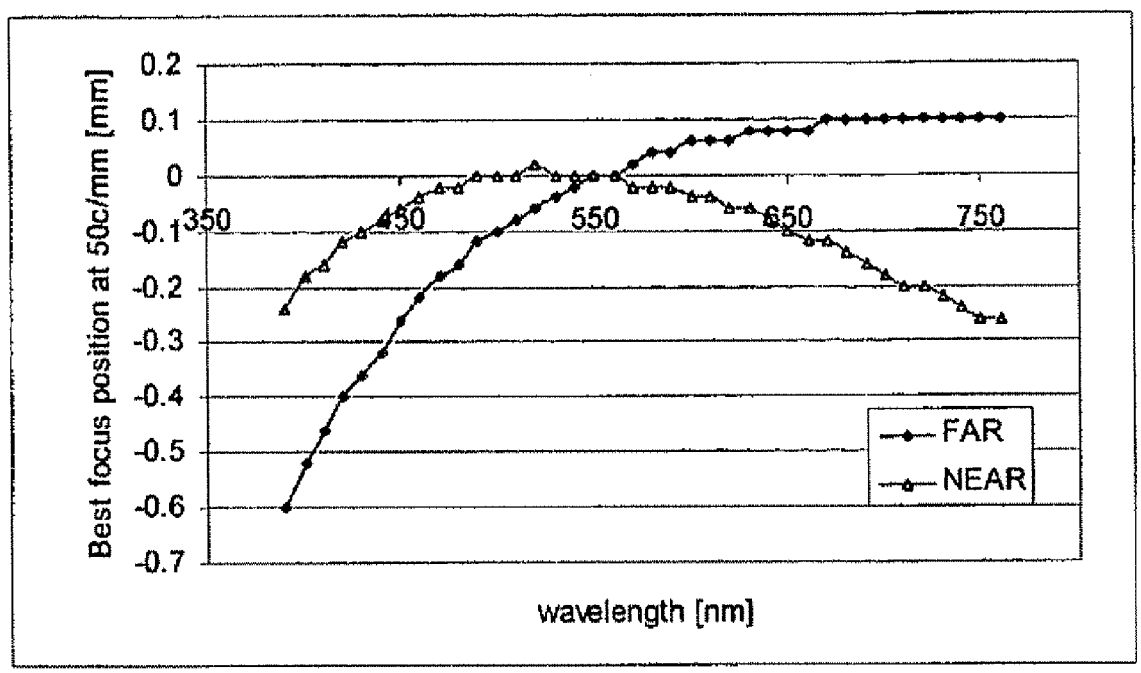

FIG. 3. shows the longitudinal chromatic aberration as a function of wavelength for the near and far focus.

Figure 4A:
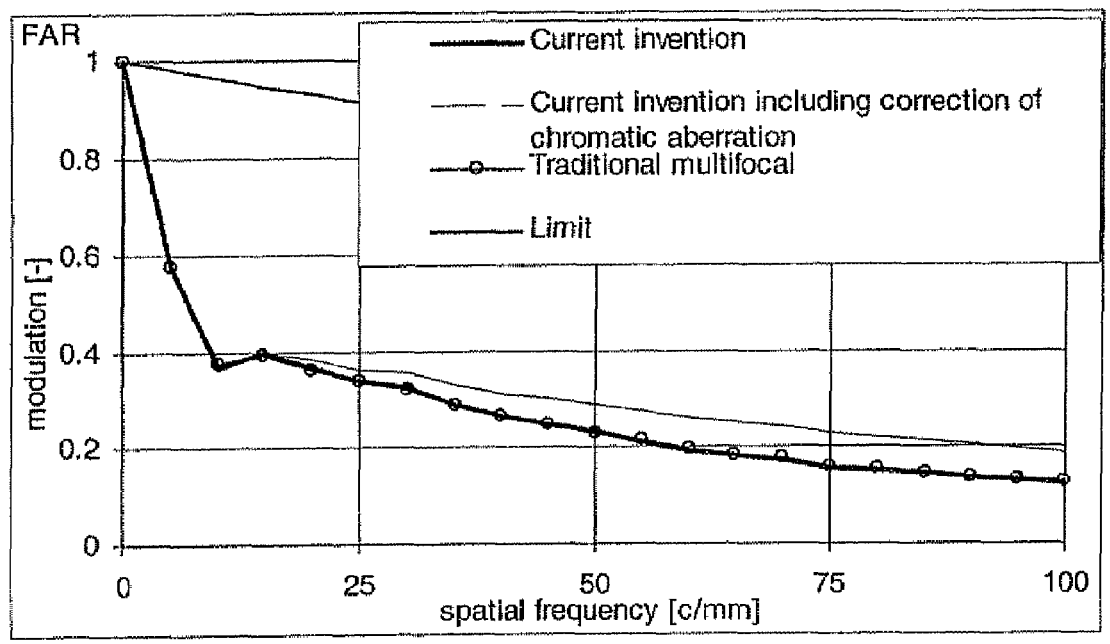
Figure 4B:
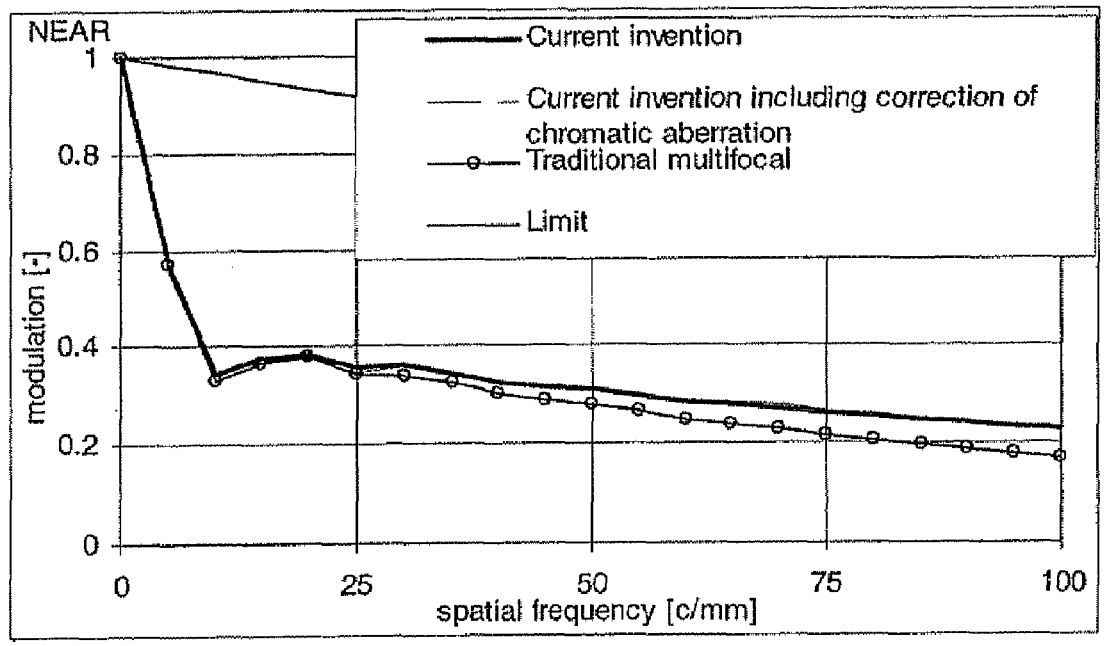

FIGS. 4A and 4B. show the Modulation Transfer Function for a bifocal intraocular lens according to two embodiments of the present invention and according to a conventional bifocal lens.

DETAILED DESCRIPTION OF PREFERRED EMBODIMENTS

The present invention generally relates to a multifocal ophthalmic lens and to methods of obtaining said multifocal intraocular lens that is capable of reducing the aberrations of the eye for at least one focus. By aberrations in this context is meant wavefront aberrations. This is based on the understanding that a converging wavefront must be perfectly spherical to form a point image, i.e. if a perfect image shall be formed on the retina of the eye, the wavefront having passed the optical surfaces of the eye, such as the cornea and a natural or artificial lens, must be perfectly spherical. An aberrated image will be formed if the wavefront deviates from being spherical. In this context the term nonspherical surface will refer to rotationally symmetric, asymmetric and/or irregular surfaces, i.e. all surfaces differing from a sphere. The wavefront aberrations can be expressed in mathematical terms in accordance with different approximate models as is explained in textbook references, such as M. R. Freeman, Optics, Tenth Edition, 1990.

In a first embodiment, the present invention is directed to a method of designing a multifocal ophthalmic lens with one base focus and at least one additional focus capable of reducing aberrations of the eye for at least one of the foci after its implantation. The base focus may also be referred to as far field focus and the at least one additional focus, as near field focus and mid field focus. The method comprises a first step of characterizing at least one corneal surface as a mathematical model, a second step wherein the mathematical model is employed for calculating the resulting aberrations of the corneal surface. An expression of the corneal aberrations is thereby obtained, i.e. the wavefront aberrations of a spherical wavefront having passed such a corneal surface. Dependent on the selected mathematical model different routes to calculate the corneal aberrations can be taken. The corneal surfaces are preferably characterized as mathematical models and the resulting aberrations of the corneal surfaces are calculated by employing the mathematical models and raytracing techniques. An expression of the corneal wavefront aberrations is thereby obtained, i.e. the wavefront aberrations of a wavefront having passed such a corneal surface. Dependent on the selected mathematical model different routes to calculate the corneal wavefront aberrations can be taken. Preferably, the corneal surfaces are characterized as mathematical models in terms of a conoid of rotation or in terms of polynomials or a combination thereof. More preferably, the corneal surfaces are characterized in terms of linear combinations of polynomials.

From the information of steps above an ophthalmic lens is modeled, such that a wavefront from an optical system comprising said lens and corneal model obtains reduced aberrations. The optical system considered when modeling the lens typically includes the cornea and said lens, but in the specific case it can also include other optical elements including the lenses of spectacles, or an artificial correction lens, such as a contact lens, a corneal inlay implant or an implantable correction lens depending on the individual situation.

Furthermore the base power for far vision, the light distribution between the at least two foci, and the optical power(s) for the additional focus/foci, of the ophthalmic lens has to be selected, which is done according to conventional methods for the specific need of optical correction of the eye, for example the method described in U.S. Pat. No. 5,968,095.

Modeling the multifocal lens involves selection of one or several lens parameters in a system which contributes to determine the lens shape for given, pre-selected refractive powers. This typically involves the selection of conventional lens parameters such as the anterior radius and surface shape, posterior radius and surface shape, the lens thickness and the refractive index of the lens, as well as parameters specific for multifocal lenses. As mentioned above there are a number of different ways by which to multifocal lenses may be designed. Hence, the multifocal specific parameters depend on what multifocal design that is used.

The multifocal ophthalmic lens according to the present invention can be realized in the form of a multifocal contact lens, a multifocal corneal inlay for aphakic patients, or the like, but it will be described in detail in the form of a multi focal intraocular lens. Furthermore the multifocal specific parameters discussed will be limited to parameters applicable on bifocal lenses of diffractive type, but it should be understood that the multifocal lens modeled according to present invention can be of any multifocal type or combinations thereof. A bifocal diffractive lens is a combination of a conventional refractive lens and a diffractive lens, the former focused to infinity and the latter for near vision. A diffractive lens consists of a series of radial rings or "zones" of decreasing width. Typically, the light distribution of a bifocal diffractive lens is set at around 50:50%, thus both the near and the far foci are accommodated. The diffractive lens may be formed on the anterior or posterior surface of the conventional lens, or at an intermediate position. The light distribution of the diffractive bifocal lens is determined by the step height of the diffractive zones. The power add for near field focus is determined by the diameters of the diffractive zones. Theoretically, this is independent of the refractive indices of the lens and the surrounding medium.

In practical terms, the lens modeling can be performed with data based on a conventional bifocal lens, such as the CeeOn® 811E lens from Pharmacia Corp. Values of the central radii of the lens, its thickness and refractive index are maintained, while selecting a different shape of the anterior and/or posterior surface, thus providing one or both of these surfaces to have a nonspherical shape.

According to one embodiment of the present invention, the anterior and/or posterior surface of the bifocal intraocular lens is modeled by selecting a suitable aspheric component. Preferably the lens has at least one surface described as a nonsphere or other conoid of rotation. Designing nonspherical surfaces of lenses is a well-known technique and can be performed according to different principles and the description of such surfaces is explained in more detail in our PCT patent application WO 01/62188, to which is given reference.

The inventive method can be further developed by comparing wavefront aberrations of an optical system comprising the lens and the model of the average cornea with the wavefront aberrations of the average cornea and evaluating if a sufficient reduction in wavefront aberrations is obtained for at least one of the foci. Suitable variable parameters are found among the above-mentioned physical parameters of the lens, which can be altered so as to find a lens model, which deviates sufficiently from being a spherical lens to compensate for the corneal aberrations.

The characterization of at least one corneal surface as a mathematical model and thereby establishing a corneal model expressing the corneal wavefront aberrations is preferably performed by direct corneal surface measurements according to well-known topographical measurement methods which serve to express the surface irregularities of the cornea in a quantifiable model that can be used with the inventive method. Corneal measurements for this purpose can be performed by the ORBSCAN® videokeratograph, as available from Orbtech, or by corneal topography methods, such as EyeSys® from Premier Laser Systems. Preferably, at least the front corneal surface is measured and more preferably both front and rear corneal surfaces are measured and characterized and expressed together in resulting wavefront aberration terms, such as a linear combination of polynomials which represent the total corneal wavefront aberrations. According to one important aspect of the present invention, characterization of corneas is conducted on a selected population with the purpose of expressing an average of corneal wavefront aberrations and designing a lens from such averaged aberrations. Average corneal wavefront aberration terms of the population can then be calculated, for example as an average linear combination of polynomials and used in the lens design method. This aspect includes selecting different relevant populations, for example in age groups, to generate suitable average corneal surfaces. Advantageously, lenses can thereby be provided which are adapted to an average cornea of a population relevant for an individual elected to undergo cataract surgery or refractive correction surgery including implantation of an IOL or corneal inlays or phakic IOLs. The patient will thereby obtain a bifocal lens that gives the eye substantially less aberrations when compared to a conventional spherical lens.

Preferably, the mentioned corneal measurements also include the measurement of the corneal refractive power. The power of the cornea and the axial eye length are typically considered for the selection of the lens power in the inventive design method.

Also preferably, the wavefront aberrations herein are expressed as a linear combination of polynomials and the optical system comprising the corneal model and modeled intraocular lens provides, for at least one of the foci and preferably for each foci, a wavefront having obtained a substantial reduction in aberrations, as expressed by one or more such polynomial terms. In the art of optics, several types of polynomials are available to skilled persons for describing aberrations. Suitably, the polynomials are Seidel or Zernike polynomials. According to the present invention Zernike polynomials preferably are employed.

The technique of employing Zernike terms to describe wavefront aberrations originating from optical surfaces deviating from being perfectly spherical is a state of the art technique and can be employed for example with a Hartmann-Shack sensor as outlined in J. Opt. Soc. Am., 1994, Vol. 11(7), pp. 1949-57. It is also well established among optical practitioners that the different Zernike terms signify different aberration phenomena including defocus, astigmatism, coma and spherical aberration up to higher aberrations. In an embodiment of the present method, the corneal surface measurement results in that a corneal surface is expressed as a linear combination of the first 15 Zernike polynomials. By means of a raytracing method, the Zernike description can be transformed to a resulting wavefront (as described in Equation (1)), wherein $Z_i$ is the i-th Zernike term and $a_i$ is the weighting coefficient for this term. Zernike polynomials are a set of complete orthogonal polynomials defined on a unit circle. Below, Table 1 shows the first 15 Zernike terms and the aberrations each term signifies.

$$z(\rho, \theta) = \sum_{i=1}^{15} a_i Z_i \quad (1)$$

In equation (1), $\rho$ and $\theta$ represent the normalized radius and the azimuth angle, respectively.

TABLE 1

| i | $Z_i(\rho, \theta)$ | |
|---|---|---|
| 1 | 1 | Piston |
| 2 | $2\rho\cos\theta$ | Tilt x |
| 3 | $2\rho\sin\theta$ | Tilt y |
| 4 | $\sqrt{3}(2\rho^2 - 1)$ | Defocus |
| 5 | $\sqrt{6}(\rho^2 \sin 2\theta)$ | Astigmatism $1^{st}$ order (45°) |
| 6 | $\sqrt{6}(\rho^2 \cos 2\theta)$ | Astigmatism $1^{st}$ order (0°) |
| 7 | $\sqrt{8}(3\rho^3 - 2\rho)\sin\theta$ | Coma y |
| 8 | $\sqrt{8}(3\rho^3 - 2\rho)\cos\theta$ | Coma x |
| 9 | $\sqrt{8}(\rho^3 \sin 3\theta)$ | Trifoil 30° |
| 10 | $\sqrt{8}(\rho^3 \cos 3\theta)$ | Trifoil 0° |
| 11 | $\sqrt{5}(6\rho^4 - 6\rho^2 + 1)$ | Spherical aberration |
| 12 | $\sqrt{10}(4\rho^4 - 3\rho^2)\cos 2\theta$ | Astigmatism $2^{nd}$ order (0°) |
| 13 | $\sqrt{10}(4\rho^4 - 3\rho^2)\sin 2\theta$ | Astigmatism $2^{nd}$ order (45°) |
| 14 | $\sqrt{10}(\rho^4 \cos 4\theta)$ | Tetrafoil 0° |
| 15 | $\sqrt{10}(\rho^4 \sin 4\theta)$ | Tetrafoil 22.5° |

Conventional optical correction with intraocular lenses will only comply with the fourth term of an optical system comprising the eye with an implanted lens. Glasses, contact lenses and some special intra ocular lenses provided with correction for astigmatism can further comply with terms five and six and substantially reducing Zernike polynomials referring to astigmatism.

The inventive method further includes to calculate the wavefront aberrations resulting from an optical system comprising said modeled bifocal intraocular lens and cornea and expressing it in a linear combination of polynomials and to determine if the bifocal intraocular lens has provided sufficient reduction in wavefront aberrations for one or more of the foci. If the reduction in wavefront aberrations is found to be insufficient, the lens will be re-modeled until one or several of the polynomial terms are sufficiently reduced. Remodeling the lens means that at least one lens design parameter affecting one or more of the foci is changed. These include the anterior surface shape and central radius, the posterior surface shape and central radius, the thickness of the lens, its refractive index, and the diameters and the step height of the diffractive zones. Typically, such remodeling includes changing the shape of a lens surface so it deviates from being spherical. There are several tools available in lens design that are useful to employ with the design method, such as the optical design software packages OSLO and Code-V. The formats of the Zernike polynomials associated with this application are listed in Table 1.

According to one embodiment, the inventive method comprises expressing at least one corneal surface as a linear combination of Zernike polynomials and thereby determining the resulting corneal wavefront Zernike coefficients, i.e. the coefficient of each of the individual Zernike polynomials that is selected for consideration. The bifocal lens is then modeled so that an optical system comprising of said model bifocal lens and cornea provides a wavefront having a sufficient reduction of selected Zernike coefficients for at least one of the foci. The method can optionally be refined with the further steps of calculating the Zernike coefficients of the Zernike polynomials representing a wavefront resulting from an optical system comprising the modeled intraocular bifocal lens and cornea and determining if the lens has provided a sufficient reduction of the wavefront Zernike coefficients for at least one foci of the optical system of cornea and lens; and optionally re-modeling said bifocal lens until a sufficient reduction in said coefficients is obtained for the at least one foci. Preferably, in this aspect the method considers Zernike polynomials up to the $4^{th}$ order and aims to sufficiently reduce Zernike coefficients referring to spherical aberration and/or astigmatism terms. It is particularly preferable to sufficiently reduce the $11^{th}$ Zernike coefficient of a wavefront from an optical system comprising cornea and said modeled multifocal intraocular lens, so as to obtain an eye sufficiently free from spherical aberration for at least one of the foci. Alternatively, the design method can also include reducing higher order aberrations and thereby aiming to reduce Zernike coefficients of higher order aberration terms than the $4^{th}$ order.

To achieve the desired reduction of aberrations, the bifocal intraocular lens is optimized with respect to unabberrated optical behavior of the optical system of the eye. In this respect, the optical behavior may be optimized for either one of the foci or both simultaneously. If the lens is optimized for the base focus, then the lens will give best optical result for far vision. Consequently when the lens is optimized for the near focus, the best performance is achieved in the near vision. Best over all performance is achieved when the lens is simultaneously optimized for both foci. The diffractive pattern of the bifocal lens may be formed independently of the lens surface that is modeled to reduce aberrations of the optical system, but it could also be formed on the same lens surface.

When designing lenses based on corneal characterizations from a selected population, preferably the corneal surfaces of each individual are expressed in Zernike polynomials describing the surface topography and there from the Zernike coefficients of the wavefront aberration are determined. From these results average Zernike wavefront aberration coefficients are calculated and employed in the design method, aiming at a sufficient reduction of selected such coefficients. In an alternative method according to the invention, average values of the Zernike polynomials describing the surface topography are instead calculated and employed in the design method. It is to be understood that the resulting lenses arriving from a design method based on average values from a large population have the purpose of substantially improving visual quality for all users. A lens having a total elimination of a wavefront aberration term based on an average value may consequently be less desirable and leave certain individuals with an inferior vision than with a conventional lens. For this reason, it can be suitable to reduce the selected Zernike coefficients only to certain degree or to a predetermined fraction of the average value. According to another approach of the inventive design method, corneal characteristics of a selected population and the resulting linear combination of polynomials, e.g. Zernike polynomials, expressing each individual corneal aberrations can be compared in terms of coefficient values. From this result, a suitable value of the coefficients is selected and employed in the inventive design method for a suitable lens. In a selected population having aberrations of the same sign such a coefficient value can typically be the lowest value within the selected population and the lens designed from this value would thereby provide improved visual quality for all individuals in the group compared to a conventional lens.

One embodiment of the method comprises selecting a representative group of patients and collecting corneal topographic data for each subject in the group. The method comprises further transferring said data to terms representing the corneal surface shape of each subject for a preset aperture size representing the pupil diameter. Thereafter a mean value of at least one corneal surface shape term of said group is calculated, so as to obtain at least one mean corneal surface shape term. Alternatively or complementary a mean value of at least one to the cornea corresponding corneal wavefront aberration term can be calculated. The corneal wavefront aberration terms are obtained by transforming corresponding corneal surface shape terms using a raytrace procedure. From said at least one mean corneal surface shape term or from said at least one mean corneal wavefront aberration term an bifocal intraocular lens capable of reducing, for at least one of its foci, said at least one mean wavefront aberration term of the optical system comprising cornea and lens is designed.

In one preferred embodiment of the present invention the method further comprises designing an average corneal model for the group of people from the calculated at least one mean corneal surface shape term or from the at least one mean corneal wavefront aberration term. It also comprises checking that the designed ophthalmic lens compensates correctly for the at least one mean aberration term. This is done by measuring these specific aberration terms of a wavefront having traveled through the model average cornea and the lens. The lens is redesigned if said at least one aberration term has not been sufficiently reduced in the measured wavefront for at least one of the foci.

Preferably one or more surface descriptive (asphericity describing) constants are calculated for the bifocal lens to be designed from the mean corneal surface shape term or from the mean corneal wavefront aberration terms for a predetermined radius. The spherical radius is determined by the refractive power of the lens.

The corneal surfaces are preferably characterized as mathematical models and the resulting aberrations of the corneal surfaces are calculated by employing the mathematical models and raytracing techniques. An expression of the corneal wavefront aberrations is thereby obtained, i.e. the wavefront aberrations of a wavefront having passed such a corneal surface. Dependent on the selected mathematical model different routes to calculate the corneal wavefront aberrations can be taken. Preferably, the corneal surfaces are characterized as mathematical models in terms of a conoid of rotation or in terms of polynomials or a combination thereof. More preferably, the corneal surfaces are characterized in terms of linear combinations of polynomials.

In one embodiment of the invention, the at least one non-spherical surface of the bifocal lens is designed such that the lens for at least one focus, in the context of the eye, provides to a passing wavefront at least one wavefront aberration term having substantially the same value but with opposite sign to a mean value of the same aberration term obtained from corneal measurements of a selected group of people, to which said patient is categorized. Hereby a wavefront arriving from the cornea of the patient's eye obtains a reduction in said at least one aberration term provided by the cornea after passing said bifocal lens. The used expression 'in the context of the eye' can mean both in the real eye and in a model of an eye.

In a specific embodiment of the invention, the wavefront obtains reduced aberration terms expressed in rotationally symmetric Zernike terms up to the fourth order. For this purpose, the surface of the bifocal intraocular lens is designed to reduce a positive spherical aberration term of a passing wavefront for at least one of the foci. In this text positive spherical aberration is defined such that a spherical surface with positive power produces positive spherical aberration. Preferably the bifocal lens is adapted to compensate for spherical aberration for at least one of the foci, and more preferably it is adapted to compensate for at least one term of a Zernike polynomial representing the aberration of a wavefront, preferably at least the $11^{th}$ Zernike term, see Table 1.

The selected groups of people could for example be a group of people belonging to a specific age interval, a group of people who will undergo a cataract surgical operation or a group of people who have undergone corneal surgery including but not limited to LASIK (laser in situ keratomileunsis), RK (radialo keratoectomy) or PRK (photorefractive keratoectomy). The group could also be a group of people who have a specific ocular disease or people who have a specific ocular optical defect.

The lens is also suitably provided with optical powers. This is done according to conventional methods for the specific need of optical correction of the eye. Preferably the refractive power for the base focus of the lens is less than or equal to 34 diopters and the additional focus between 2 and 6 diopters. An optical system considered when modeling the lens to compensate for aberrations typically includes the average cornea and said lens, but in the specific case it can also include other optical elements including the lenses of spectacles, or an artificial correction lens, such as a contact lens, a corneal inlay or an implantable correction lens depending on the individual situation.

In an especially preferred embodiment the bifocal intraocular lens is designed for people who will undergo a cataract surgery. In this case it is has been shown that the average cornea from such a population is represented by a prolate surface following the formula:

$$z = \frac{\left(\frac{1}{R}\right)r^2}{1+\sqrt{1-\left(\frac{1}{R}\right)^2(cc+1)r^2}} + adr^4 + aer^6$$

wherein,
the conical constant cc has a value ranging between −1 and 0
R is the central lens radius and
ad and ae are polynomial coefficients additional to the conical constant.

In these studies the conic constant of the prolate surface ranges between about −0.05 for an aperture size (pupillary diameter) of 4 mm to about −0.18 for an aperture size of 7 mm. According to these results the bifocal intraocular lens to be designed should have a prolate surface following the same formula. Accordingly a bifocal intraocular lens suitable to improve visual quality by reducing at least spherical aberration for at least one focus for a cataract patient based on an average corneal value will have a prolate surface following the formula above. Since the cornea generally produces a positive spherical aberration to a wavefront in the eye, a bifocal intraocular lens for implantation into the eye will have negative spherical aberration terms while following the mentioned prolate curve. As will be discussed in more detail in the exemplifying part of the specification, it has been found that an intraocular lens that can correct for 100% of a mean spherical aberration has a conical constant (cc) with a value of less than 0 (representing a modified conoid surface). For example, a 6 mm diameter aperture will provide a 20 diopter lens with conical constant value of about −1.02.

In this embodiment, the bifocal intraocular lens is designed to balance the spherical aberration of a cornea that has a Zernike polynomial coefficient representing spherical aberration of the wavefront aberration with a value in the interval from 0.0000698 mm to 0.000871 mm for a 3 mm aperture radius, 0.0000161 mm to 0.00020 mm for a 2 mm aperture radius, 0.0000465 mm to 0.000419 mm for a 2.5 mm aperture radius and 0.0000868 mm to 0.00163 mm for a 3.5 mm aperture radius using polynomials expressed in table 1. These values were calculated for a model cornea having two surfaces with a refractive index of the cornea of 1.3375. It is possible to use optically equivalent model formats of the cornea without departing from the scope of the invention. For example one or more multiple surface corneas or corneas with different refractive indices could be used. The lower values in the intervals are here equal to the measured average value for that specific aperture radius minus one standard deviation. The higher values are equal to the measured average value for each specific aperture radius plus three standard deviations. The reason for selecting only minus one SD (=Standard Deviation) while selecting plus three SD is that in this embodiment it is convenient to only compensate for positive corneal spherical aberration and more than minus one SD added to the average value would give a negative corneal spherical aberration.

According to one embodiment of the invention the method further comprises the steps of measuring the at least one wavefront aberration term of one specific patient's cornea and determining if the selected group corresponding to this patient is representative for this specific patient. If this is the case the selected lens is implanted and if this is not the case a lens from another group is implanted or an individual lens for this patient is designed using this patient's corneal description as a design cornea. These method steps are preferred since then patients with extreme aberration values of their cornea can be given special treatments.

According to another embodiment, the present invention is directed to the selection of a bifocal intraocular lens of refractive powers, suitable for the desired optical correction that the patient needs, from a plurality of lenses having the same powers but different aberrations. The selection method is similarly conducted to what has been described with the design method and involves the characterizing of at least one corneal surface with a mathematical model by means of which the aberrations of the corneal surface is calculated. The optical system of the selected lens and the corneal model is then evaluated so as to consider if sufficient a reduction in aberrations is accomplished for at least one foci by calculating the aberrations of a wavefront arriving from such a system. If an insufficient correction is found a new lens is selected, having the same powers, but different aberrations. The mathematical models employed herein are similar to those described above and the same characterization methods of the corneal surfaces can be employed.

Preferably, the aberrations determined in the selection are expressed as linear combinations of Zernike polynomials and the Zernike coefficients of the resulting optical system comprising the model cornea and the selected lens are calculated. From the coefficient values of the system, it can be determined if the bifocal intraocular lens has sufficiently balanced the corneal aberration terms for at least one foci, as described by the Zernike coefficients of the optical system. If no sufficient reduction of the desired individual coefficients is found, these steps can be iteratively repeated by selecting a new lens of the same powers but with different aberrations, until a lens capable of sufficiently reducing the aberrations of the optical system for at least one foci is found. Preferably at least 15 Zernike polynomials up to the $4^{th}$ order are determined. If it is regarded as sufficient to correct for spherical aberration, only the spherical aberration terms of the Zernike polynomials for the optical system of cornea and bifocal intraocular lens are corrected. It is to be understood that the bifocal intraocular lens shall be selected so a selection of these terms become sufficiently small for the optical system comprising lens and cornea for at least one of the foci. In accordance with the present invention, the $11^{th}$ Zernike coefficient, $a_{11}$, can be substantially eliminated or brought sufficiently close to zero for at least one of the foci. This is a prerequisite to obtain a bifocal intraocular lens that sufficiently reduces the spherical aberration of the eye for at least one of the foci. The inventive method can be employed to correct for other types of aberrations than spherical aberration by considering other Zernike coefficients in an identical manner, for example those signifying astigmatism, coma and higher order aberrations. Also higher order aberrations can be corrected dependent on the number of Zernike polynomials elected to be a part of the modeling, in which case a lens can be selected capable of correcting for higher order aberrations than the $4^{th}$ order.

According to one important aspect, the selection method involves selecting lenses from a kit of lenses having lenses with a range of powers and a plurality of lenses within each power combinations for far and near foci having different aberrations. In one example the lenses within each power combination have anterior surfaces with different aspherical components. If a first lens does not exhibit sufficient reduction in aberration for at least one of the foci, as expressed in suitable Zernike coefficients, then a new lens of the same power combination, but with a different surface (aspheric component) is selected. The selection method can if necessary be iteratively repeated until the best lens is found or the studied aberration terms are reduced below a significant borderline value for at least one of the foci. In practice, the Zernike terms obtained from the corneal examination will be directly obtained by the ophthalmic surgeon and by means of an algorithm they will be compared to known Zernike terms of the lenses in the kit. From this comparison the most suitable lens in the kit can be found and implanted. Alternatively, the method can be conducted before cataract surgery and data from the corneal estimation is sent to a lens manufacturer for production of an individually tailored lens.

The present invention further pertains to a bifocal intraocular lens having at least one nonspherical surface capable of transferring, for at least one foci, a wavefront having passed through the cornea of the eye into a substantially spherical wavefront with its center at the retina of the eye. Preferably, the wavefront is substantially spherical with respect to aberration terms expressed in rotationally symmetric Zernike terms up to the fourth order.

In accordance with an especially preferred embodiment, the invention relates to a bifocal intraocular lens, which has at least one surface, when expressed as a linear combination of Zernike polynomial terms using the normalized format, that has a negative 11th term of the fourth order with a Zernike coefficient $a_{11}$ that that can balance a positive corresponding term of the cornea, to obtain sufficient reduction of the spherical aberration for at least one foci of the eye after implantation. In one aspect of this embodiment, the Zernike coefficient $a_{11}$ of the bifocal lens is determined so as to compensate for an average value resulting from a sufficient number of estimations of the Zernike coefficient $a_{11}$ in several corneas. In another aspect, the Zernike coefficient $a_{11}$ is determined to compensate for the individual corneal coefficient of one patient. The bifocal lens can accordingly be tailored for an individual with high precision.

The invention further relates to another method of providing a patient with a bifocal intraocular lens, which at least partly compensates for the aberrations of the eye for at least one of the foci. This method comprises removing the natural lens from the eye. Surgically removing of the impaired lens can be performed by using a conventional phacoemulsification method. The method further comprises measuring the aberrations of the aphakic eye, not comprising the a lens, by using a wavefront sensor. Suitable methods for wavefront measurements are found in J. Opt. Soc. Am., 1994, Vol. 11(7), pp. 1949-57 by Liang et. al. Furthermore, the method comprises selecting from a kit of lenses a lens that at least partly compensates for the measured aberrations for at least one of the foci and implanting said lens into the eye. The kit of lenses comprises lenses of different powers and different aberrations and finding the most suitable lens can be performed in a manner as earlier discussed. Alternatively, an individually designed lens for the patient can be designed based on the wavefront analysis of the aphakic eye for subsequent implantation. This method is advantageous, since no topographical measurements of the cornea are need to be done and the whole cornea, including the front and back surfaces, is automatically considered.

According to a special embodiment of the present invention the aspheric multifocal lenses designed to reduce aberrations of wavefronts in the foci arriving from a system of the lens and cornea, as described in the foregoing parts, can provided with means to distribute light among the foci with purpose of providing the wearer of the lens with a better functional vision. For example, it is desirable to provide the far focus of an aspheric bifocal aberration reducing IOL with more light intensity when the pupil is its maximum diameter. In practical terms this will provide an individual with better visual quality of distant objects in darkness, so driving during night is simplified. There are several known techniques to modify the light distribution of multifocal lenses by reducing the step height of the diffractive pattern in the direction towards the periphery of lens. U.S. Pat. No. 4,881,805 suggests different routes to use different echelette depth to vary the light intensity among the different foci of a multifocal lens. U.S. Pat. No. 5,699,142 discloses a multifocal intraocular lens with a diffractive pattern having an apodization zone that gradually shifts the energy balance from the near focus to the distant focus. The apodization zone is construed so that the echelettes of the diffractive pattern gradually has a reduced depth towards the lens periphery. By making an appropriate adjustment of the step height (echelette depth), a desired deviation from 50-50% distribution between the two foci of a bifocal lens can be obtained.

According to another special embodiment, the aspheric multifocal lenses of the present invention as outlined in the previous parts of the specification can be provided with means to reduce chromatic aberration in at least one of its foci. Aspheric monofocal lenses with a capacity to correct both chromatic aberration and other aberrations as induced by the optical parts of the eye and distort vision has been described in the International patent application published as WO 02/084281 which hereby is incorporated as a reference. In this context "chromatic aberration" signifies both monochromatic and chromatic aberration introduced by the optical surfaces of eye and eventually also the lens itself.

The multifocal intraocular lenses can generally be of a refractive or a diffractive type of the diffractive type has been described elsewhere in greater detail. For both alternatives of multifocal IOLs, the chromatic aberration preferably is provided by a surface configured as a diffractive part with a diffractive surface pattern and has a refractive power to be added to the total lens power. In both alternatives, chromatic aberration reducing surface is designed to compensate for any chromatic aberration introduced by the refractive part of lens and for monochromatic aberrations introduced by said diffractive surface pattern. As is discussed in WO 02/084281, it is possible to design the lens to reduce chromatic aberration determined from individual eye surface (i.e. corneas), or to reduce an averaged chromatic aberration value collected from relevant group of individuals (e.g. a mean value from corneas of patients elected to undergo cataract surgery).

In the design process of an aspheric multifocal IOL that is capable of correcting both for chromatic aberrations and other aberrations, such as spherical aberrations, it may also be needed to compensate for other aberrations, such as spherical aberrations introduced by the diffractive pattern, while performing optional adjustments of the power contribution of the diffractive pattern.

For the example where the asphericity compensate for aberration terms, such as spherical aberration the features providing the lens with multiple foci already are set, the design process preferably would include the steps of:
(i) selecting an eye model, suitably the eye model of Navarro (1985), with an aspheric multifocal ophthalmic lens of a predetermined refractive power and a predetermined amount of at least one monochromatic aberration;
(ii) estimating the power of said eye model at different wavelengths, so as to determine the chromatic aberration of the eye model;
(iii) estimating a correction function of how the power varies with the wavelength to be an ideal compensation for said chromatic aberration of the eye model;
(iv) finding a linear function of how power varies with the wavelength, which suitably approximates said correction function;
(v) calculating a provisional zone width of a diffractive profile corresponding to this linear function and also calculating the diffractive power of this diffractive profile;
(vi) reducing the refractive power of the lens by the amount of power calculated for the diffractive profile;
(vii) estimating a new correction function of step iii), finding a new linear function of step iv) and calculating a new provisional zone width and a new diffractive power for a new diffractive profile corresponding to this new linear function;
(viii) adjusting the refractive power of the lens such that the total power equals the predetermined power;
(ix) repeating steps vii) to viii) until a suitable combination of a refractive and a diffractive part of the hybrid ophthalmic lens is found that both provide the eye model with a predetermined power and with a suitable reduction in chromatic aberration.

In the design process it is preferable for a diffractive bifocal lens to balance the chromatic aberration between the near and the distant foci in a manner that resulting lens in a Navarro eye model obtains polychromatic modulation transfer functions at 50 cycles/mm from a set eye model which approaches the same value (see also Example 4, below)

For the embodiment with a diffractive aspheric multifocal IOL, the diffractive surface pattern correcting for chromatic aberration will be a second diffractive pattern that consists of a number of rings. For the example, a lens having a total 2 D power with a 2 D power coming from the second diffractive pattern, the first zone has a radial width of 1.5 mm. In this case, the second diffractive surface pattern is located on the anterior side of the lens superimposed on the spherical surface. Preferably, the first diffractive pattern then is located on the posterior side of the lens. Also, for a refractive bifocal lens, the chromatic aberration is (slightly) different for the near and far focus, which means that the performance of the near and far focus can be balanced, using a merit function, of which the modulation transfer functions at 50 c/mm is an example.

In another special embodiment, the multifocal lens modeled to reduce aberrations of at least of the foci in a optical system comprising the lens and a model cornea without taking considerations to aberrations that the cornea will provide a wavefront with when passing the system. This type of lenses will be suitable for individuals with corneas that generate few aberrations or when there is not access to any corneal aberration data. These lenses will be designed with a nonspherical surface with a surface design construed to reduce aberrations in a wavefront passing said lens that are generated from the lens itself. Typically, such aberrations involve spherical aberration. A suitable example of this type of multifocal lens is of the diffractive type having a diffractive pattern on the lens surface that is capable of generating multiple foci, and more preferably it is a bifocal lens that distributes more light to its distant focus than to its near focus. Optionally, it can be provided with the mentioned means to generate a desired light distribution and with a second diffractive pattern to compensate for chromatic aberrations of the eye The lenses according to the present invention can be manufactured with conventional methods. In one embodiment they are made from soft, resilient material, such as silicones or hydrogels. Examples of such materials suitable for foldable intraocular lenses are found in U.S. Pat. No. 5,444,106 or in U.S. Pat. No. 5,236,970. Manufacturing of nonspherical silicone lenses or other foldable lenses can be performed according to U.S. Pat. No. 6,007,747. Alternatively, the lenses according to the present invention can be made of a more rigid material, such as poly(methyl)methacrylate. The skilled person can readily identify alternative materials and manufacturing methods, which will be suitable to employ to produce the inventive aberration reducing lenses.

As is shown in the following examples, the bifocal intraocular lens according to the present invention (BRAIOL) outperforms conventional BIOLs with respect to Modulation Transfer Function characteristics. More specifically it has been found that the BRAIOL has a modulation of at least 0.2 for both foci at a spatial frequency of 50 cycles per millimeter, when designed such that the light distribution between the two foci is 50:50%. The measurements are performed in an average eyemodel using a 5 mm aperture. Surprisingly it has further been found that the sum of the modulation at 50 c/mm for the two or more foci is more than 0.40, and in some cases even above 0.50, independent of the light distribution, when measured in the model specified above. The fact that the sum of the modulation at 50 c/mm is independent of light distribution is illustrated for the case where the light distribution has a limiting value of 100:0%, which is equivalent to a monofocal lens. Conventional lenses and lenses correcting spherical aberration were designed, manufactured and measured. In this situation, the conventional lens has a modulation at 50 c/mm of 0.21, while the design optimized for spherical aberration shows a modulation of 0.6, equivalent to the sum of the designed bifocal lens.

Furthermore, the evaluation experiments have revealed that the wavefronts of the 2 foci of a bifocal lens are independent with respect to some of the Zernike terms, but that some of the Zernike terms are coupled or equal for both. The far majority of this difference is in the 'defocus' term, which represents the 4 diopters difference between the focal points. In the design process it has been found that the spherical aberration part of the wavefront is not very different for the 2 wavefronts. This is also true for all other aberrations, apart from defocus, tilt and the piston term. Consequently the present invention makes it possible to provide a lens with reduced aberrations in essentially the same scale for all foci.

EXAMPLES

General:

A bifocal intraocular lens which corrects the corneal spherical aberration (BRAIOL) can be modeled based on a conventional bifocal lens (BIOL), in this case the bifocal model 811E, Pharmacia Corp., which is a diffractive lens design made of Poly(MethylMethAcrylate) material. The power add of this lens is +4 diopter for reading, which corresponds to reading spectacles of 3 diopters. In this example, the design is adapted to be used for a silicone material. As a consequence, the step heights of the diffractive surface profile are increased with the ratio of the reduced refractive indices of the 2 materials.

The lens optic is a combination of a biconvex lens and a diffractive lens. The diffractive surface profile is superimposed onto the spherical posterior surface of the optic. The diffractive surface profile can be described using conventional sag equations. Examples of equations for the surface profile are described in the literature. For instance, Cohen (1993, 'Diffractive bifocal lens design', Optom Vis Sci 70(6): 461:8) describes the diffractive profile with the equation:

$$S_d(r) = h * \{N - r^2/w^2\}$$

wherein
r is the distance from the optical axis
h is the maximum profile height (stepheight)
N is the zone number
w is the width of the first zone Other equations are also possible. The type of diffractive profile is not relevant for the working principles. The diffractive profile is superimposed onto a normal spherical surface, so that the total sag equation becomes $$S(r) = S_s(r) + S_d(r),$$

where $S_s(r)$ is the sag equation of a spherical biconvex lens:

$$S_s(r) = \frac{cv * r^2}{1 + \sqrt{1 - cv^2 * r^2}}$$

cv=1/R is the curvature of the lens optic
R is the radius of curvature of the lens optic The radius of curvature of the diffractive bifocal lens is equal to the radius of curvature of a monofocal lens having the same power.

Throughout the example the tight distribution between the two foci was chosen to be 50%:50%, and the target power add for near vision was +4 D. Other light distributions can be chosen, without changing the principles of how the methods work. In practice, light distribution between 70%:30% to 30%:70% and near vision add between 3 and 4 diopters have been on the market. But also outside these ranges the methods should be applicable.

Throughout the example, data from characterization of corneas conducted on a selected population, was used to calculate the resulting corneal aberrations. The anterior corneal surface shapes of a population of 71 cataract patients were measured using corneal topography. The surface shapes were described using Zernike polynomials. Each surface shape was converted into a wavefront aberration. Also the wavefront aberration was described in Zernike polynomials.

The method is described in example 4 of the patent application WO 01/89424 A1.

The terms of the Zernike polynomials are expressed in wavelengths ($\lambda$), using the reference wavelength of 550 nanometers ($\lambda$=550 nm).

The target in this example is to correct the corneal spherical aberration by the bifocal IOL. In order to evaluate the designs, a theoretical design cornea was developed, similar to the one described in example 4 of the patent application WO 01/89424 A1. In the case of modelling a monofocal IOL the design cornea can be a 1-surface model, wherein the refractive index of the cornea is the keratometry index of 1.3375. For diffractive lenses it is essential to use the real in vivo refractive index surrounding the posterior (diffractive) lens surface. Therefore, a 2-surface model was developed, which has the same on-axis aberrations as the 1-surface model.

The theoretical performance of the prototype design in terms of symmetric Zernike coefficients was evaluated for an IOL having a base power (far vision) of 20 Diopters. An IOL having this power is close to what is suitable for most cataract patients. However, the design method and resulting IOL is similar for other lens powers. Typically, IOL powers range from 4 to 34 diopters, sometimes extend to $-10$ to $+40$ diopters and can be occasionally produced even outside these ranges.

Example 1

In one embodiment, the lens is biconvex, having radii of curvature of 12.15 mm on both the anterior and posterior surface and a central thickness of 1.1 mm. The anterior surface is aspherized. In an iterative process, the aberration of the optical system of design cornea and bifocal IOL are optimised in order to reduce the wavefront aberration in the far focus position, in this example the Zernike term $Z_{11}$, representing the spherical aberration. In this process, the asphericity of the anterior lens surface is used as the design parameter. The asphericity of the anterior surface is described by a conic constant. The sag equation of the anterior surface is:

$$S(r) = \frac{cv * r^2}{1 + \sqrt{1 - cv^2(cc+1)r^2}}$$

wherein cc is the conic constant

Using commercially available optical design software, the variable cc can be optimized to minimize the Zernike term $Z_{11}$ for the far vision focal point. The variable cc was determined for an aperture size of 5.1 mm. The anterior surface of this BRAIOL has been modified in such a way that the spherical aberration of the system (cornea+lens) is now approximately equal to 0. The resulting value of the conic constant was $-29.32$. The $Z_{11}$ coefficient representing spherical aberration for the conventional IOL in the eye model is 3.8$\lambda$, while the same coefficient for the eye model with the designed BRAIOL is 0.01$\lambda$, representing a reduction of the spherical aberration by a factor of 380. The same process as described above for can similarly be performed for any other lens power.

Example 2

In another embodiment, the lens is biconvex, having radii of curvature of 12.15 mm on both the anterior and posterior surface and a central thickness of 1.1 mm. The diffractive posterior surface is aspherized. In an iterative process, the aberration of the optical system of design cornea and bifocal IOL are optimised in order to reduce the wavefront aberration, in this example the Zernike term $Z_{11}$, representing the spherical aberration, as well as the symmetrical higher order terms $Z_{22}$ and $Z_{37}$. In this process, the asphericity of the posterior lens surface is used as the design parameter. The asphericity of the posterior surface is described by a conic constant and 2 higher order terms. The total sag equation is:

$$S(r) = \frac{cv*r^2}{1+\sqrt{1-cv^2(cc+1)r^2}} + ad*r^4 + ae*r^6 + S_d(r)$$

wherein:
cc is the conic constant
ad is the $4^{th}$ order aspheric coefficient
ae is the $6^{th}$ order aspheric coefficient Using commercially available optical design software, the variables cc, ad and ae can be optimized to minimize the Zernike terms $Z_{11}$, $Z_{22}$ and $Z_{37}$ simultaneously in the far focal point. The variables are determined for an aperture size of 5.1 mm. The posterior surface of this BRAIOL has been modified in such a way that the spherical aberration and the 2 higher order terms of the system (cornea+lens) is now approximately equal to 0. The optimisation resulted in the posterior surface aspheric coefficients presented in table 2:

TABLE 2

| Aspheric coefficient | Value |
| --- | --- |
| Cc | −2.53 |
| Ad | 9.4e−4 |
| Ae | −5.1e−6 |

The optical results can be expressed as a reduction in the Zernike coefficients between the conventional BIOL (using cc=ad=ae=0) and the newly designed BRAIOL, and are presented in table 3:

TABLE 3

| Zernike coefficient | Conventional BIOL | BRAIOL |
| --- | --- | --- |
| $Z_{11}$ | 3.8 λ | 0.01 λ |
| $Z_{22}$ | 0.11 λ | −0.003 λ |
| $Z_{37}$ | −0.07 λ | −0.07 λ |

Table 3 shows a large reduction of aberration represented by the coefficients $Z_{11}$ and $Z_{22}$ and no significant reduction of coefficient $Z_{37}$. The same process as described above for can similarly be performed for any other lens power.

Example 3

Both

In another embodiment, the lens is biconvex, having an anterior radius of curvature of 12.15 mm, a posterior radius of curvature of 12.59 and a central thickness of 1.1 mm. The diffractive profile is located on the posterior surface and the anterior surface is aspherized. In an iterative process, the aberration of the optical system of design cornea and bifocal IOL are optimised in order to reduce the wavefront aberration, in this example the Zernike term $Z_{11}$, representing the spherical aberration, as well as the symmetrical higher order terms $Z_{22}$ and $Z_{37}$. In this process, the asphericity of the anterior lens surface is used as the design parameter. The asphericity of the anterior surface is described by a conic constant and 2 higher order terms. The sag equation of the anterior surface is:

$$S(r) = \frac{cv*r^2}{1+\sqrt{1-cv^2(cc+1)r^2}} + ad*r^4 + ae*r^6$$

wherein:
cc is the conic constant
ad is the $4^{th}$ order aspheric coefficient
ae is the $6^{th}$ order aspheric coefficient Using commercially available optical design software, the variables cc, ad and ae can be optimized to minimize the Zernike term $Z_{11}$, $Z_{22}$ and $Z_{37}$ simultaneously. Furthermore, in this embodiment the Zernike terms for both far and near focal points were taken into account in the optimisation. In this way both far and near focal point were optimised simultaneously. As an extra criterion, weight factors were added, to secure that the lowest order terms were reduced most drastically. The weight factors were 1, 0.1 and 0.01 for $Z_{11}$, $Z_{24}$ and $Z_{37}$ respectively. The variables are determined for an aperture size of 5.1 mm. The posterior surface of this BRAIOL has been modified in such a way that the spherical aberration and the 2 higher order terms of the system (cornea+lens) is now approximately equal to 0. The optimisation resulted in the posterior surface aspheric coefficients, presented in table 4:

TABLE 4

| Aspheric coefficient | Value |
| --- | --- |
| cc | −1.02 |
| ad | −4.9e−4 |
| ae | −4.9e−5 |

The optical results can be expressed as a reduction in the Zernike coefficients between the conventional BIOL (using cc=ad=ae=0) and the newly designed BRAIOL. Since both far and near are taken into account, the vector sum of the far and near Zernike coefficients are displayed in table 5:

TABLE 5

| Zernike coefficient | Conventional BIOL | BRAIOL |
| --- | --- | --- |
| $Z_{11}$ | 5.3 λ | 0.08 λ |
| $Z_{22}$ | 0.15 λ | 0.43 λ |
| $Z_{37}$ | 0.08 λ | 0.08 λ |

Table 5 shows a large reduction of aberration represented by the coefficients $Z_{11}$ and no significant reduction of coefficient $Z_{22}$ and $Z_{37}$, indicating that Zernike term $Z_{11}$ was minimized on the cost of term $Z_{22}$, while $Z_{37}$ was as low as reasonably possible already.

The optical quality was further characterized by calculating the modulation transfer function in the eye model, using an aperture of 5 mm (FIG. 1)

These calculation results show that, when compared with a conventional BIOL, the modulation transfer function of the BRAIOL is increased with at least by a factor 2. Prototype lenses of this design were made and the modulation transfer function was also measured in an eye model. The physical eye model was constructed to have the same wavefront aberrations as the design model based on the population of 71 cataract patients. The focal points were determined by focusing at a spatial frequency of 25, 50, 100 cycles per millimetre. FIG. 2 shows the results. The results are the averages of 8 BRIOL lenses and 10 conventional BIOL lenses, with 3 measurements per lens. The FIG. 2 confirms the gain in optical quality that can be achieved with the BRAIOL.

This example clearly shows that the RAIOL design principles can be successfully applied on bifocal (or multifocal) lenses. Three approaches were used: one design with the anterior lens shape optimized for Zernike coefficient $Z_{11}$ for far focus combined with a diffractive posterior surface. Alternatively a new posterior lens shape was generated by optimizing the wavefront aberrations of Zernike coefficients $Z_{11}$, $Z_{22}$ and $Z_{37}$. Finally, a new anterior lens shape was generated by optimizing for the Zernike coefficients $Z_{11}$, $Z_{22}$ and $Z_{37}$ and for the far as well as the near focus. The performance of these 3 types of lenses, in terms of MTF, showed to be essentially comparable. It was also demonstrated that the improvement optical performance as calculated in theory can be confirmed by measurement of prototype lenses.

The improvement of the BRAIOL, compared to BIOL (model 811E), is significant. However the improvement is greater for the larger pupils (larger than 3 mm).

The optical form chosen for the new BRAIOL design is an equiconvex lens made from a silicone with refractive index of 1.458. The spherical aberration of an average cornea is balanced by the BRAIOL lens yielding a system without spherical aberration. The front surface of the lens is modified such that the optical path lengths of all on-axis rays within the design aperture are the same producing a point focus. This feature can be achieved with many lens forms. The BRAIOL lens could therefore be designed on a convex-plano, plano-convex, non-equiconvex lens or any other design yielding a positive lens. The BRAIOL concept could also be extended in order to encompass a negative lens used to correct the refractive errors of the eye. The front surface or back surface could also be modified to produce the needed change in optical path difference that neutralizes the spherical aberration. There are therefore many possible designs that would achieve the goals of the BRAIOL lens design.

Example 4

Chromatic Correction of Multifocal Aspheric Intraocular Lenses

The correction of chromatic aberration is performed by a diffractive lens. A diffractive multifocal lens already has a diffractive profile in its surface. For a bifocal diffractive lens, this diffractive profile only has an effect on one of the focal points, usually the near focus. This means that for the near focus, the chromatic aberration is already reduced in some degree, although this was not originally intended.

The chromatic correction by a diffractive lens influences both focal points to an (almost) equal amount. Since for bifocal diffractive lenses, the amount of chromatic aberration is not the same in both focal points, the amount of chromatic aberration have to be balanced between the two focal points.

Description of the Lens:

The example lens is made of silicone material. Its shape is equi-biconvex. The anterior surface of the lens comprises an aspheric refractive lens, on which a diffractive profile is superimposed. The diffractive profile has a lens power of 2.0 diopters, while the aspheric refractive lens has a lens power of 18.0 D. The total resulting lens power is 20 diopters. The width (diameter) of the first zone of the diffractive profile is 1.5 mm, and there are 16 rings needed to fill a full 6.0 mm IOL optic. In the periphery of the lens, the diffractive rings are 94 microns apart from each other.

The posterior surface includes the normal diffractive profile which generates a 4 diopter power add in the near focus.

Eye dimensions, refractive indices and dispersion of the ocular media are used as described by Navarro (1985). This eyemodel includes an aspheric cornea. The surface information for the eye model and the lens is given in Table 6. The lens designed is dependent on the eye model chosen. It must be noted that it is possible to design lenses using other eye models of actual physiological data from patients.

TABLE 6

| SRF | RADIUS | THICKNESS | APERTURE RADIUS | MEDIUM | NOTE |
|---|---|---|---|---|---|
| OBJ | — | 1.00E+20 | 1.00E+14 | AIR | |
| 1 | 7.72 | 0.55 | 2.55 | CORNEA | ASPHERE |
| 2 | 6.5 | 3.05 | 2.50 | AQUEOUS | |
| AST | — | — | 2.25 | AQUEOUS | |
| 4 | — | 0.9 | 2.25 | AQUEOUS | |
| 5 | 13.511 | 1 | 2.18 | SILICONE | ASPHERE, DIFFRACTIVE |
| 6 | −13.511 | 18.30 | 2.08 | VITREOUS | DIFFRACTIVE |
| IMS | −12 | 0 | 1 | — | RETINA |

| CONIC AND POLYNOMIAL ASPHERIC DATA | | | |
|---|---|---|---|
| Surface | conic constant | AD | AE |
| 1 | −0.260000 | — | — |
| 5 | −1.018066 | −0.000509 | −4.0423e−06 |

*DIFFRACTIVE SURFACE DATA (symmetric diffractive surface)

| Surface | Diffraction order | Design λ | Kinoform construction order | Kinoform zone depth | DF0 | DF1 |
|---|---|---|---|---|---|---|
| 5 | 1 | 0.550 μm | 1 | 0.004561 | — | −0.001 |

Behavior of the Lens:

38 discrete wavelengths over the visible spectrum of 390 to 760 nm (10 μm steps) were used to evaluate the eyemodel including the refractive/diffractive IOL.

The focus point is here defined as the point where the polychromatic MTF (Modulation Transfer Function) has its maximum at 50 cycles/mm. The polychromatic MTF is determined by the weighed average of the MTF results at all wavelengths used. The weighting of the wavelengths was determined by the standard luminance of the eye under photopic light conditions, which represents the relative sensitivity of the retina for different wavelengths. The actual back focal length (ABFL) values for the different wavelengths indicate the presence of a chromatic difference in focus and by definition the amount of longitudinal chromatic aberration. The calculations are performed at a 3.0 mm aperture (pupil). FIG. 3 shows the change in focal point versus the wavelength. The 2 graphs, for far and near vision, are coupled by the 4 diopter diffractive power add. Especially for wavelengths higher than 550 nm, this example design shows a good balance between the chromatic aberration of the far and the near focal point.

Table 7 and FIGS. 4A and 4B show the modulations at 50 cycles per millimeters for a spherical lens diffractive bifocal lens, a diffractive bifocal lens with an aspherical anterior surface and a diffractive bifocal lens with an aspherical anterior surface with also the chromatic aberration corrected by a 2.0 D monofocal diffractive pattern on the anterior surface. The chromatic correction mainly influences the FAR focal point, since the NEAR focal point is already (in part) corrected by the diffractive bifocal surface.

TABLE 7

|  | monochromatic MTF at 50 c/mm | | | polychromatic MTF at 50 c/mm | | |
| --- | --- | --- | --- | --- | --- | --- |
|  | FAR | NEAR | Limit | FAR | NEAR | Limit |
| Spherical | 0.33 | 0.30 | 0.83 | 0.23 | 0.28 | 0.83 |
| Aspherical | 0.34 | 0.34 | 0.83 | 0.23 | 0.31 | 0.83 |
| Aspherical, chromatic corrected | 0.33 | 0.34 | 0.83 | 0.29 | 0.31 | 0.83 |

A number of embodiments have been described above. However, it is obvious that the design could be varied without deviating from the inventive idea of providing a multifocal ophthalmic lens correcting aberration in the eye system.

Therefore the present invention should not be regarded as restricted to the above disclosed embodiments, but can be varied within the scope of the appended claims. For example, the BIOL can be designed to compensate for non-symmetrical Zernike terms. This would require making surfaces being rotationally non-symmetric, which is within the state of the art production techniques, demonstrated by cylindrical lenses being currently on the market.

The invention claimed is:

1. A method of designing a multifocal ophthalmic lens, comprising:
   selecting a representative group of patients;
   for the group, determining at least one of an average corneal shape and an average corneal spherical aberration;
   modeling a lens comprising:
      an anterior surface and an opposing posterior surface;
      a diffractive pattern on one of the surfaces configured to generate multiple foci, the diffractive pattern characterized by a plurality of zones having predetermined diameters and the step heights; and
      an aspheric shape on one of the surfaces, the aspheric surface being described by a radius of curvature and a conic constant; and
   selecting the radius of curvature, the conic constant, the predetermined diameters, and the step heights to compensate for the average corneal spherical aberration and to reduce an averaged chromatic aberration for the group.

2. The method of claim 1, wherein the aspheric surface and the diffractive pattern are on a common surface.

3. The method of claim 1, wherein the diffraction pattern is configured to produce an apodization zone in which the step heights are selected to reduce towards the periphery of the lens.

4. The method of claim 1, wherein the diffractive pattern includes an apodization zone configured to gradually shift energy from a first focus of the multifocal lens to a second focus of the multifocal lens.

5. The method of claim 1, wherein a light distribution between the base focus and the additional focus is between 70%:30% to 30%:70%.

6. The method of claim 1, further comprising the steps of:
   designing an average corneal model for the group of people from the calculated at least one mean corneal surface shape term or from the at least one mean corneal wavefront aberration term; and
   checking that the designed multifocal ophthalmic lens compensates correctly for the at least one mean aberration term for at least one of the foci by measuring these specific aberration terms of a wavefront having traveled through the model average cornea and the lens and redesigning the multifocal lens if the at least one aberration term not has been sufficiently reduced in the measured wavefront.

7. The method of claim 1, further comprising selecting people in a specific age interval to constitute the group of people.

8. The method of claim 1, further comprising selecting people who will undergo a cataract surgery to constitute the group of people.

9. The method of claim 1, further comprising designing the lens specifically for a patient that has undergone corneal surgery and therefore selecting people who have undergone corneal surgery to constitute the group of people.

10. The method of claim 1, further comprising selecting people who have a specific ocular disease to constitute the group of people.

11. The method of claim 1, further comprising selecting people who have a specific ocular optical defect to constitute the group of people.

12. The method of claim 1, further comprising the steps of:
   measuring the at least one wavefront aberration term of one specific patient's cornea; and
   determining if the selected group corresponding to this patient is representative for this specific patient and, if this is the case, implanting the multifocal lens designed from these average values and, if this is not the case, implanting a multifocal lens designed from average values from another group or designing an individual lens for this patient.

13. The method of claim 1, further comprising providing the multifocal lens with at least one non-spherical surface that reduces at least one positive spherical aberration term of an incoming non-spherical wavefront for at least one of the foci.

14. The method of claim 1, wherein the ophthalmic lens is an intraocular lens.

15. A method of designing a multifocal ophthalmic lens, comprising:

selecting a representative group of patients;

for the group, determining at least one of an average corneal shape and an average corneal spherical aberration;

modeling a lens comprising:

an anterior surface and an opposing posterior surface;

a diffractive pattern on one of the surfaces configured to generate multiple foci, the diffractive pattern characterized by a plurality of zones having predetermined diameters and the step heights; and an aspheric shape on one of the surfaces, the aspheric surface being described by a radius of curvature and a conic constant; and selecting the radius of curvature, the conic constant, the predetermined diameters, and the step heights to reduce for the average corneal spherical aberration and an averaged chromatic aberration for the group.

16. The method of claim 15, wherein the aspheric surface and the diffractive pattern are on a common surface.

17. The method of claim 15, wherein the diffraction pattern is configured to produce an apodization zone in which the step heights are selected to reduce towards the periphery of the lens.

18. The method of claim 15, wherein a light distribution between the base focus and the additional focus is between 70%:30% to 30%:70%.

19. The method of claim 15, further comprising selecting people in a specific age interval to constitute the group of people.

20. The method of claim 15, wherein the ophthalmic lens is an intraocular lens.

* * * * *